United States Patent [19]

Hunkeler et al.

[11] 4,352,816
[45] Oct. 5, 1982

[54] AZETO-IMIDAZO-DIAZEPINES AND THEIR USE

[75] Inventors: Walter Hunkeler, Magden; Emilio Kyburz, Reinach, both of Switzerland

[73] Assignee: Hoffmann-La Roche Inc., Nutley, N.J.

[21] Appl. No.: 349,405

[22] Filed: Feb. 16, 1982

[30] Foreign Application Priority Data

Feb. 27, 1981 [CH] Switzerland .......................... 1339/81

[51] Int. Cl.³ .................. A61K 31/55; C07D 513/22; C07D 487/14
[52] U.S. Cl. .................. 424/273 R; 260/239.3 T; 260/239.3 P; 260/239 A; 260/330.3
[58] Field of Search ............. 260/239.3 P; 424/273 R

[56] References Cited
U.S. PATENT DOCUMENTS 4,316,832 2/1982 Gerecke et al. ............. 260/239.3 T Primary Examiner—Robert T. Bond
Attorney, Agent, or Firm—Jon S Saxe; Bernard S. Leon; Frank P. Hoffman

[57] ABSTRACT

There is presented imidazodiazepines of the formula

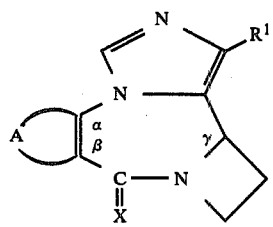

wherein A together with the two carbon atoms denoted as $\alpha$ and $\beta$ is the group

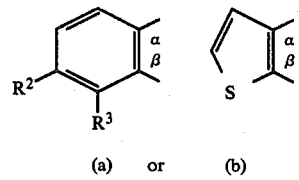

(a) or (b)

$R^1$ is hydrogen, lower alkyl, lower alkoxymethyl, halogen, nitro or a group of the formula —COOR⁴, $R^2$ is hydrogen, trifluoromethyl or halogen, $R^3$ is hydrogen, trifluoromethyl, halogen or lower alkyl, $R^4$ is methyl, ethyl or isopropyl and X is an oxygen or sulphur atom and the carbon atom denoted as $\gamma$ has the (S)- or (R,S)-configuration, and their pharmaceutically acceptable acid addition salts.

The compounds are useful in the antagonization of the central-depressant, muscle relaxant, ataxic, blood pressure-lowering and respiratory-depressant properties of 1,4-benzodiazepines which have tranquillizing activity. They can also be used for suppressing the activities on the central nervous system of 1,4-benzodiazepines used in other fields of therapy, for example, of schistosomicidally-active 1,4-benzodiazepines. Also provided are methods to produce the above compounds.

8 Claims, No Drawings

AZETO-IMIDAZO-DIAZEPINES AND THEIR USE

DESCRIPTION OF THE INVENTION

The present invention is concerned with imidazodiazepines. More particularly, the invention is concerned with imidazodiazepines of the formula

I wherein A together with the two carbon atoms denoted as α and β is the group (a) or (b)

$R^1$ is hydrogen, lower alkyl, lower alkoxymethyl, halogen, nitro or a group of the formula —$COOR^4$, $R^2$ is hydrogen, trifluoromethyl or halogen, $R^3$ is hydrogen, trifluoromethyl, halogen or lower alkyl, $R^4$ is methyl, ethyl or isopropyl and X is an oxygen or sulphur atom and the carbon atom denoted as γ has the (S)- or (R,S)-configuration, and pharmaceutically acceptable acid addition salts thereof.

Objects of the present invention are compounds of formula I and pharmaceutically acceptable acid addition salts thereof per se and as pharmaceutically active substances, the manufacture of these compounds and intermediates for the manufacture of these compounds, medicaments containing a compound of formula I or a pharmaceutically acceptable acid addition salt thereof and the manufacture of such medicaments.

The term "lower alkyl" denotes saturated hydrocarbon groups, which can be straight-chain or branched-chain, containing at most 7, preferably at most 4, carbon atoms such as methyl, ethyl, isopropyl, t-butyl and the like. The term "lower alkoxymethyl" includes groups such as methoxymethyl, ethoxymethyl and the like. The term "halogen" signifies fluorine, chlorine, bromine and iodine.

$R^1$ preferably is hydrogen, chlorine or a group of the formula —$COOR^4$ in which $R^4$ preferably is ethyl. The symbol A preferably is group (a) hereinbefore: in this case $R^2$ preferably is hydrogen and $R^3$ preferably is hydrogen or chlorine. The symbol X preferably is an oxygen atom.

A quite especially preferred compound of formula I is ethyl (S)-8-chloro-12,12a-dihydro-9-oxo-9H,11H-azeto[2,1-c]imidazo[1,5-a][1,4]benzodiazepine-1-carboxylate.

Other compounds of formula I which are especially preferred are:
Ethyl (R,S)-12,12a-dihydro-9-oxo-9H,11H-azeto[2,1-c]imidazo[1,5-a][1,4]benzodiazepine-1-carboxylate,
(S)-8-chloro-12,12a-dihydro-9H,11H-azeto[2,1-c]imidazo[1,5-a][1,4]benzodiazepin-9-one,
ethyl (S)-12,12a-dihydro-9-oxo-9H,11H-azeto[2,1-c]imidazo[1,5-a][1,4]benzodiazepine-1-carboxylate and
(S)-1-chloro-12,12a-dihydro-9H,11H-azeto[2,1-c]imidazo[1,5-a][1,4]benzodiazepin-9-one.

The imidazodiazepines of formula I and their pharmaceutically acceptable acid addition salts can be manufactured in accordance with the invention by
(a) Reacting a compound of the formula

II wherein A is as above and Z is a leaving group, in the presence of a base with an isocyanoacetic ester of the formula $$CN-CH_2-COOR^4 \quad III$$

wherein $R^4$ is as above, or
(b) treating a compound of the formula

IV wherein A and $R^4$ are as above, with a formylating agent, or
(c) dehydrogenating a compound of the formula V or VI wherein A and $R^4$ are as above or
(d) replacing the amino group in an amino compound of the formula

VII wherein A and X are as above by a halogen atom or by the nitro group, or (e) oxidizing the amino group in an amino compound of formula VII above to the nitro group, or (f) decarboxylating a carboxylic acid of the formula

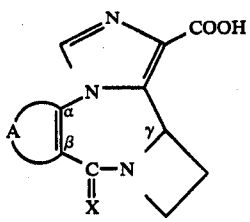   VIII wherein A and X are as above or (g) halogenating a compound of the formula

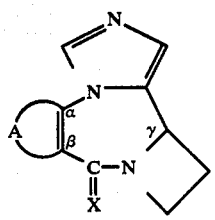

wherein A and X are as above in the imidazole ring, or (h) cleaving off under reductive conditions the leaving group denoted by Z' in a compound of the formula

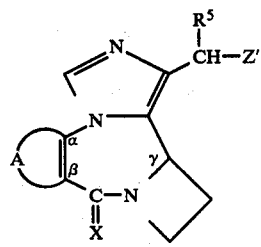   IX wherein A and X are as above, $R^5$ is hydrogen or lower alkyla and Z' is a leaving group, or (i) trans-esterifying a compound of the formula

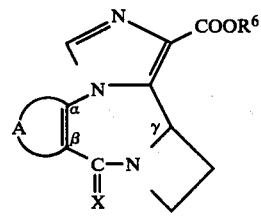   Ib wherein A and X are as above and $R^6$ is lower alkyl, or (j) converting the carbonyl group in a compound of the formula

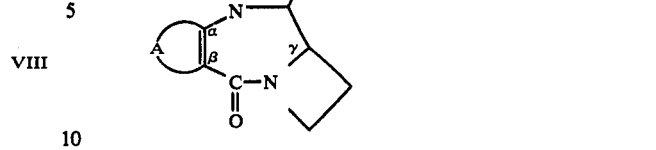   Ic wherein $R^1$ and A are as above, into the thiocarbonyl group, or (k) etherifying a compound of the formula

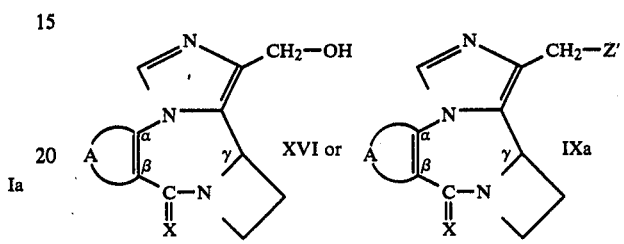   XVI or   IXa wherein A, X and Z' are as above with an alkylating agent yielding a lower alkyl group in the case of a compound of formula XVI or with a lower alcohol in the case of a compound of formula IXa, and (1) if desired, converting a compound of formula I obtained into a pharmaceutically acceptable acid addition salt.

In accordance with process variant (a), compounds of formula I can be manufactured from compounds of formula II and isocyanoacetic esters of formula III. The leaving group denoted by Z in formula II is, for example, a readily cleavable phosphinyl group, e.g. a group of the formula

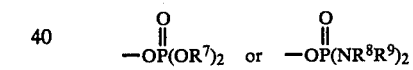

wherein $R^7$ is lower alkyl and $R^8$ and $R^9$ each are lower alkyl, allyl, phenyl or substituted phenyl or $R^8$ and $R^9$ together with the nitrogen atom are an unsubstituted or substituted heterocyclic ring with 3–8 members (such as morpholine), a halogen atom, an alkylthio group, an aralkylthio group, a N-nitrosoalkylamino group, an alkoxy group, a mercapto group and the like (when Z is a mercapto group, then the corresponding compound of formula II is the iminothiol form of the corresponding thiolactam). The reaction of a compound of formula II with a compound of formula III is carried out in an inert solvent such as dimethylformamide, hexamethylphosphoric acid triamide, dimethyl sulphoxide, tetrahydrofuran or any other suitable organic solvent and in the presence of a base which is sufficiently strongly basic to form the anion of the isocyanoacetic ester of formula III. Suitable bases are alkali metal alkoxides such as sodium methoxide or potassium t-butoxide, alkali metal hydrides such as sodium hydride, alkali metal amides such as lithium amide or lithium diisopropylamide, tertiary amine such as triethylamine, and the like. The reaction is conveniently carried out at a temperature between about −40° C. and about room temperature.

In accordance with process variant (b), compounds of formula I can be manufactured by treating compounds of formula IV with a formylating agent. Suitable formylating agents for this process variant are lower alkyl esters of orthoformic acid and technical equivalents thereof, for example ortho-amides such as N,N-dimethylformamide dimethyl acetal, N,N,N',N',N'',N''-hexamethylmethanetriamine and the like. The reaction of a compound of formula IV with a formylating agent is conveniently carried out in the presence of an acid catalyst, for example an organic or inorganic acid such as p-toluenesulphonic acid, phosphoric acid and the like, and at room temperature or at a temperature above room temperature, for example between about 25° and about 150° C.

In accordance with process variant (c), compounds of formula I can be manufactured by dehydrogenating compounds of formula V or VI. Preferred reagents for this dehydrogenation include manganese dioxide, palladium-on-carbon and elemental oxygen, with atmospheric oxygen being sufficient. However, potassium permanganate, for example, can also be used. Solvents in which this dehydrogenation can be carried out include chlorinated hydrocarbons such as methylene chloride and chloroform, aromatic hydrocarbons, dimethylformamide etc. The dehydrogenation is carried out at room temperature or at a temperature above room temperature, conveniently between about 25° and about 200° C.

In accordance with process variant (d), compounds of formula I in which $R^1$ is halogen or nitro can be manufactured by replacing the amino group in a compound of formula VII by a halogen atom or by the nitro group. Conveniently, the amino compound of formula VII is converted into a corresponding diazonium salt and this is reacted, optionally without previous isolation, with a nitrite such as sodium nitrite or with a halide (e.g. with a chloride or bromide) in the presence of a copper (I) salt. The presence of a copper (I) salt is not necessary for the manufacture of the corresponding iodides. Corresponding fluorides are conveniently manufactured via a corresponding diazonium tetrafluoroborate, for example by irradiation with UV light. These reactions are preferably carried out in aqueous solutions at temperatures of about $-10°$ C. to about room temperature.

In accordance with process variant (e), compounds of formula I in which $R^1$ is nitro can also be manufactured by oxidizing an amino compound of formula VII. Suitable oxidizing agents are, for example, peracids such a peracetic acid, trifluoroperacetic acid, m-chloroperbenzoic acid and perbenzoic acid, and the like. As solvents there come into consideration, depending on the oxidizing agent used, carboxylic acids such as acetic acid etc, halogenated hydrocarbons such as methylene chloride, chloroform, 1,2-dichloroethane etc, or the like. As a rule, the oxidation is carried out at a temperature of about 0° C. to about room temperature.

In accordance with process variant (f), compounds of formula I in which $R^1$ is hydrogen can be manufactured by decarboxylating carboxylic acids of formula VIII. This decarboxylation is conveniently carried out by dry heating the carboxylic acid of formula VIII, which may be crude, to temperatures of about 150° C. to about 400° C., the temperature depending on the melting point of the particular compound of formula VIII used.

In accordance with process variant (g), compounds of formula I in which $R^1$ is halogen can be manufactured by halogenating compounds of formula Ia. Suitable halogenating agents are, for example, N-chlorosuccinimide, N-bromosuccinimide, N-chloroacetamide, N-bromoacetamide and elemental iodine. As solvents there are conveniently used inert organic solvents, for example halogenated hydrocarbons such as methylene chloride, 1,2-dichloroethane, chloroform and the like, dimethylformamide, dimethylacetamide, acetonitrile, ethers such as diethyl ether, tetrahydrofuran, dioxan and the like, etc. The halogenation can be carried out in a temperature range of about 0° C. to about 120° C. depending on the solvent used.

In accordance with process variant (h), compounds of formula I in which $R^1$ is lower alkyl can be manufactured by cleaving off under reductive conditions the leaving group denoted by Z' in a compound of formula IX. This process variant is carried out according to methods known per se, the choice of the suitable leaving group denoted by Z' as well as the determination of the conditions suitable for the cleavage, under which other structural elements present in the molecule should not be affected, presenting no difficulties to a person skilled in the art. Especially suitable leaving groups for the present process variant are, for example, halogen atoms such as chlorine, bromine and iodine which can be cleaved off readily under hydrogenolytic conditions, for example by treatment with elemental hydrogen in the presence of a suitable catalyst (e.g. palladium/carbon, Raney-nickel, etc.) in an inert organic solvent. Suitable solvents are, for example, alcohols such as methanol, ethanol and isopropanol, ethers such as diethyl ether, tetrahydrofuran, dioxan and dimethoxyethane, and the like. Depending on the reactivity of the catalyst used the cleavage is carried out at pressures of about normal pressure to about 300 bar and at temperatures of about room temperature to about 150° C.

In accordance with process variant (i), compounds of formula I can be manufactured by trans-esterifying compounds of formula Ib, i.e. by replacing the alkyl group denoted by $R^6$ in a compound of formula Ib by the desired group $R^4$.

This trans-esterificaton is carried out in a manner known per se by reacting a compound of formula Ib with an alcohol corresponding to the desired group denoted by $R^4$ (i.e. with methanol, ethanol or isopropanol) at room temperature or while heating to a temperature of about 25° to 150° C. Preferably, the trans-esterification is carried out in the presence of a base, with potassium cyanide or similar weak bases being especially suitable in the present case. As the base there is, however, also suitable the alcoholate corresponding to the desired group denoted by $R^4$, for example, sodium methanolate, ethanolate or isopropanolate or the corresponding potassium salt. As the solvent there is preferably used the alcohol corresponding to the group denoted by $R^4$ in the desired compound of formula I. However, the trans-esterification can also be carried out in an inert organic solvent, for example an aromatic hydrocarbon such as benzene or xylene, an ether such as dioxan, tetrahydrofuran or ethyleneglycol dimethyl ether, dimethylformamide, dimethyl sulphoxide or the like. In this trans-esterification not only can a low boiling alcohol be replaced by a high boiling alcohol, but also a high boiling alcohol can be replaced by a low boiling alcohol.

The trans-esterification can, however, also be carried out readily in several stages, for example, by hydrolyzing a compound of formula Ib to the corresponding free carboxylic acid of formula VIII, preparing from this a reactive functional derivative (e.g. an acid chloride or the like) and subsequently reacting this reactive carboxylic acid derivative with the alcohol corresponding to the significance of $R^4$ in the desired compound of formula I.

In accordance with process variant (j), compounds of formula Ic can be converted into corresponding compounds of formula I in which X is a sulphur atom by treatment with a sulphurizing agent, which can be carried out in a manner known per se. For example, the sulphurizing agent can be phosphorus pentasulphide, this being preferably used in excess and the reaction being advantageously carried out in an inert organic solvent such as dioxan, methylene chloride or the like in the presence of triethylamine at a temperature of about 50° C. up to the reflux temperature of the reaction mixture. Other suitable sulphurizing agents are compounds such as 2,4-bis(p-methoxyphenyl)-1,3,2,4-dithiaphosphetane-2,4-disulphide; such sulphurizing agents being used in approximately the calculated amount and the reaction being carried out in the presence of an inert solvent such as toluene or xylene, conveniently at the reflux temperature of the reaction mixture, or in hexamethylphosphoric acid triamide at a temperature between about 60° and 110° C.

In accordance with process variant (k), compounds of formula I in which $R^1$ is lower alkoxymethyl can be manufactured by etherifying an alcohol of formula XVI with an alkylating agent yielding a lower alkyl group or etherifying a compound of formula IXa with a lower alcohol. This etherification is carried out in an inert organic solvent such as dimethylformamide, hexamethylphosphoric acid triamide, dimethyl sulphoxide, tetrahydrofuran or any other suitable organic solvent and in the presence of a base which is sufficiently strongly basic to form the corresponding alcoholate from the alcohol of formula XVI or from the lower alcohol. Suitable bases are, for example, alkali metal hydrides such as sodium hydride, alkali metals such as sodium and alkali metal amides such as lithium amide and lithium diisopropylamide. Suitable alkylating agents are, for example, alkyl halides such as methyl iodide, ethyl iodide and ethyl bromide and dialkyl sulphates such as dimethyl sulphate and diethyl sulphate. This etherification is conveniently carried out at a temperature between about 0° C. and about 50° C.

In accordance with process variant (l), compounds of formula I can be converted into pharmaceutically acceptable acid addition salts. The manufacture of such pharmaceutically acceptable acid addition salts is carried out according to generally usual methods. The salts provided by the present invention are salts formed with inorganic acids and organic acids; for example, hydrochlorides, hydrobromides, sulphates, methanesulphonates, p-toluenesulphonates, oxalates and the like.

The compounds of formula II used as starting materials can be prepared starting from compounds of the general formula

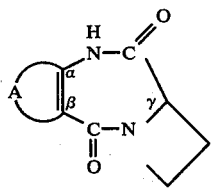

X wherein A is as above according to methods which are known per se; see, for example, Belgian Patent Specification Nos. 802 233, 833 249 and 865 653, American Patent Specification No. 3 681 341 and J. Org. Chemistry 29, 231 (1964), incorporated herein for reference purposes.

Various Examples hereinafter contain detailed information concerning the preparation of compounds of formula II from compounds of formula X.

The compounds of formula X, in turn, can be prepared readily according to methods known per se; for example, by reacting a corresponding carboxylic acid anhydride of the formula

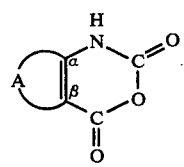

XI wherein A is as above with (L)- or (D,L)-azetidinecarboxylic acid.

It is also possible to react a compound of the formula

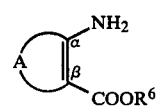

XII wherein A and $R^6$ are as above with a reactive derivative of a carboxylic acid of the formula

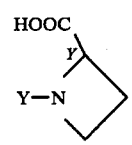

XIII wherein Y is a protecting group, for example a carboxylic acid chloride or the like. After removing the protecting group denoted by Y from a thus-obtained compound of the formula

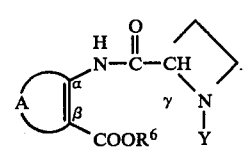

XIV wherein $R^6$, A and Y are as above and cyclizing the substance obtained (e.g. by heating to temperatures of about 100° to about 300° C. for a short time), there is obtained a compound of formula X.

The compounds of formulae IV, V and VI can be prepared according to methods known per se (see Belgian Patent Specifications Nos. 883 248 and 839 364), incorporated herein for reference, starting from compounds of formula II in accordance with Formula Scheme 1 hereinafter in which A, $R^4$ and Z are as above.

Formula Scheme 1

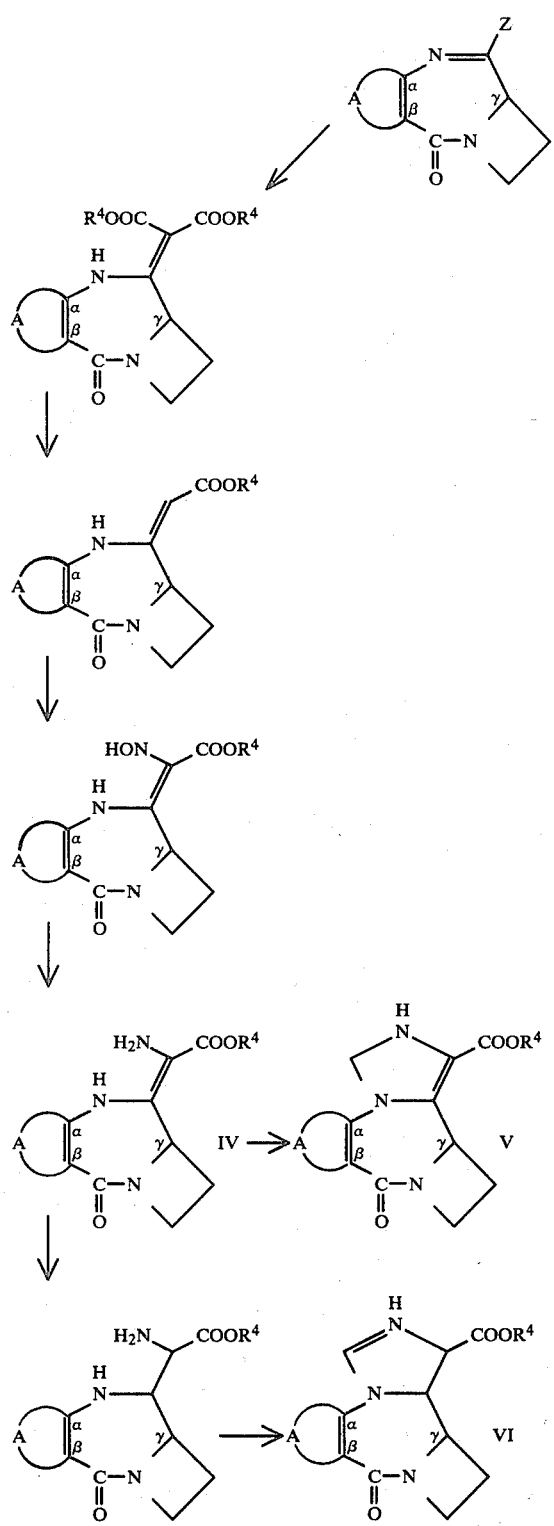

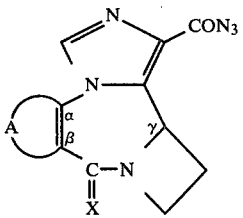

wherein A and X are as above, for example, by treating such an azide with an alcohol (e.g. methanol, ethanol, benzyl alcohol or the like) at an elevated temperature and hydrolyzing the urethane obtained. In a preferred embodiment, benzyl alcohol is used and the benzylurethane obtained is cleaved hydrogenolytically.

The carboxylic acid azides of formula XV can be prepared, for example, by treating a carboxylic acid ester of formula Ib with hydrazine and reacting the carboxylic acid hydrazide obtained with sodium nitrite in the presence of an acid such as acetic acid.

The compounds of general formula VII used as starting materials can be readily prepared by hydrolyzing carboxylic acid esters of formula Ib. Conveniently, the hydrolysis is carried out in basic aqueous solution, for example in aqueous sodium hydroxide, optionally in the presence of a solubilizer (e.g. methanol, ethanol, tetrahydrofuran, dioxan or the like). If the compound of formula Ib is a t-alkyl ester (e.g. a t-butyl ester), then the hydrolysis is conveniently carried out under acidic conditions; for example, using trifluoroacetic acid, aqueous mineral acids or the like.

The compounds of formula IX used as starting materials are readily accessible from carboxylic acid esters of formula Ib in accordance with Formula Scheme 2 hereinafter in which A, X, Z' and $R^6$ are as above and $R^{51}$ is lower alkyl:

Formula Scheme 2

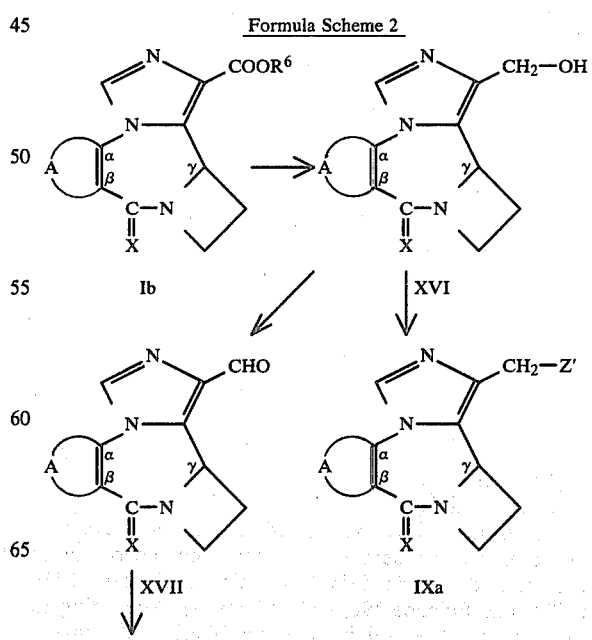

The amino compounds of formula VII used as starting materials can be prepared, for example, in a manner known per se from the carboxylic acid azides of the formula -continued
Formula Scheme 2

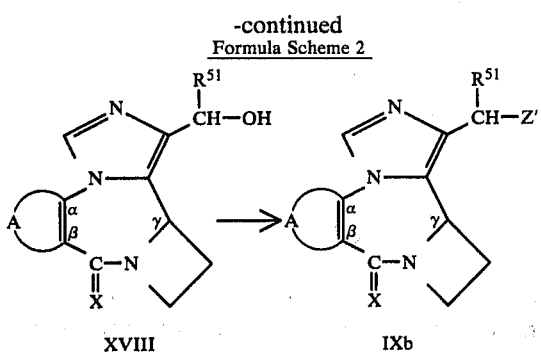

The reduction of a compound of formula Ib to give an alcohol of formula XVI is preferably carried out using a reducing agent such as lithium borohydride in an inert organic solvent such as diethyl ether, tetrahydrofuran, dimethoxyethane or the like.

The preparation of a compound of formula XVII from an alcohol of formula XVI is preferably carried out using a mild oxidizing agent such as manganese dioxide or the like in an inert organic solvent such as methylene chloride, chloroform or the like.

The compounds of formula XVIII can be prepared by reacting a compound of formula XVII with a metal-organic compound yielding the group $R^{51}$ according to methods which are generally known and familiar to any person skilled in the art. Preferred metal-organic compounds are Grignard compounds such as methyl-magnesium iodide, ethyl-magnesium iodide, isopropyl-magnesium bromide, n-propyl-magnesium bromide, n-butyl-magnesium chloride and the like. Suitable solvents are ethers such as diethyl ether, tetrahydrofuran, t-butyl methyl ether, mixtures thereof and the like. Conveniently, the reaction is carried out at the boiling point of the reaction mixture, although it can, however, also be carried out at a lower temperature (e.g. at room temperature).

The compounds of formula IX (i.e. formula IXa and IXb) can be prepared from compounds of formula XVI or XVIII according to methods which are generally known and familiar to any person skilled in the art. Corresponding halides are obtained, for example, by treating compounds of formula XVI or XVIII with halogenating agents such as thionyl chloride, phosphorus oxychloride, phosphorus pentachloride, carbon tetrabromide/triphenylphosphine and the like.

The compounds of formulae II, IV, V, VI, VII, VIII, IX and XVI used as starting materials are novel and are likewise objects of the present invention.

The compounds of formula Ib in which $R^6$ is not methyl, ethyl, isopropyl or t-butyl are likewise an object of the present invention.

As mentioned earlier, the compounds of formula I are novel and have extremely valuable pharmacodynamic properties. They exhibit only a low toxicity and it has been shown that they have a pronounced affinity to the central benzodiazepine receptors and are capable of antagonizing the central-depressant, muscle relaxant, ataxic, blood pressure-lowering and respiratory-depressant properties of 1,4-benzodiazepines which have tranquillizing activity.

The affinity of compounds of formula I to the central benzodiazepine receptors was determined according to the method described in Life Science 20, 2101–2110 (1977) and Science 198, 849–851 (1977). According to this method, the inhibition of the binding of tritiated diazepam at the specific benzodiazepine receptors in the cerebral cortex by the respective test substances is ascertained. The $IC_{50}$ ("50% inhibiting concentration") is that concentration of the respective test substance which brings about a 50 percent inhibition of the specific binding of the tritiated diazepam at the specific benzodiazepine receptors in the cerebral cortex.

One of the typical properties of 1,4-benzodiazepines, which have tranquillizing activity, in experimental animals is their pronounced anticonvulsant activity which can be demonstrated, for example, in the known and generally recognized pentetrazole test. This property was used to evaluate the test described hereinafter which permits the determination of compounds which are capable of antagonizing the central properties of 1,4-benzodiazepines which have tranquillizing activity.

In this test, 5 mg/kg (i.p.) of diazepam (i.e. a supramaximal dosage which in the pentetrazole test on more than 900 mice protects all experimental animals from convulsive attacks) were administered to mice 1 hour before the pentetrazole (120 mg/kg i.p.) and the compound to be tested was administered p.o. 15 minutes before the pentetrazole. The antagonistic activity of the compounds investigated, i.e. their ability to counteract the activity of the diazepam in the pentetrazole test, is determined by counting the mice which suffer convulsive attacks in this test.

In the following Table there are presented the results which have been obtained with representative members of the class of compound defined by formula I in the test previously described. The $ED_{50}$ value is given for each of the compounds listed in the Table. The $ED_{50}$ is the amount of test compound in mg/kg (p.o.) which in 50% of the animals counteracts the diazepam effect in the above test. Moreover, the Table contains the $IC_{50}$ value (defined above) for all test compounds listed therein.

TABLE

| Compound of formula I | | | | | $IC_{50}$ in nM/l | $ED_{50}$ in mg/kg p.o. |
|---|---|---|---|---|---|---|
| A | $R^2$ $R^3$ | $R^1$ | X | Configuration | | |
| (a) | H H | —COOCH$_2$CH$_3$ | O | (R,S) | 3.0 | 5.4 |
| (a) | H H | —COOCH$_2$CH$_3$ | O | (S) | 1.3 | 3.7 |
| (a) | H H | Cl | O | (S) | 37.0 | 6.9 |
| (a) | H Cl | —COOCH$_2$CH$_3$ | O | (S) | 0.99 | 0.75 |
| (a) | H Cl | H | O | (S) | 150 | 15.8 |

As mentioned earlier, the compounds of formula I antagonize the central-depressant, muscle relaxant, ataxic, blood pressure-lowering and respiratory-depressant properties of 1,4-benzodiazepines which have tranquillizing activity. The latter are in widespread use in therapy and are often administered in high dosages, so that the above-mentioned activities can also appear strongly as side-effects. The compounds of formula I can be used as antidotes in the case of intoxications in which excessive intake of 1,4-benzodiazepines which have tranquillizing activity is concerned. They are also suitable for shortening anaesthesia in surgery and in obstetrics induced by 1,4-benzodiazepines which have tranquillizing activity. In the case of neonatals, a possible respiratory depression, which deteriorates upon the administration of 1,4-benzodiazepines which have tranquillizing activity to the mother, can be counteracted. The compounds of formula I can also be used to suppress, in the case of 1,4-benzodiazepines which are used in other fields of indication, the activities on the central nervous system which are undesirable in such a case.

Examples of such 1,4-benzodiazepines which can be used in other fields of indication are the schistosomicidally-active 1,4-benzodiazepines described in British Patent Specifications Nos. 1 444 529 and 1 474 305 such as (+)-5-(o-chlorophenyl)-1,3-dihydro-3-methyl-7-nitro-2H-1,4-benzodiazepin-2-one.

The compounds of formula I and their pharmaceutically acceptable acid addition salts can be used as medicaments, for example, in the form of pharmaceutical preparations. The pharmaceutical preparations can be administered orally (e.g. in the form of tablets, coated tablets, dragees, hard and soft capsules, solutions, emulsions or suspensions). The administration can, however, also be carried out rectally (e.g. in the form of suppositories) or parenterally (e.g. in the form of injection solutions).

For the manufacture of tablets, coated tablets, dragees and hard gelatine capsules, the compounds of formula I and their pharmaceuticaly acceptable acid addition salts can be processed with pharmaceutical inert inorganic or organic carriers. Examples of such carriers which can be used for tablets, dragees and hard gelatine capsules are lactose, maize starch or derivatives thereof, talc, stearic acid or its salts etc. Suitable carriers for soft gelatine capsules are, for example, vegetable oils, waxes, fats, semi-solid and liquid polyols etc. Suitable carriers for the manufacture of solutions and syrups are, for example, water, polyols, saccharose, invert sugar, glucose and the like. Suitable carriers for injection solutions are, for example, water, alcohols, polyols, glycerine, vegetable oils etc. Suitable carriers for suppositories are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, colouring agents, flavouring agents, salts for varying the osmotic pressure, buffers, coating agents or antioxidants. They can also contain still other therapeutically valuable substances.

As mentioned earlier, compounds of general formula I and pharmaceutically acceptable acid addition salts thereof can be used in accordance with the invention in the control or prevention of illnesses, especially in the antagonization of the central-depressant, muscle relaxant, ataxic, blood pressure-lowering and respiratory-depressant properties of 1,4-benzodiazepines which have tranquillizing activity. In particular, compounds of formula I can be used in combination with the schistosomicidally-active compounds mentioned above, for example, in combination with (+)-5-(o-chlorophenyl)-1,3-dihydro-3-methyl-7-nitro-2H-1,4-benzodiazepin-2-one, in the control of schistosomiasis. In this case, the compounds of formula I or their pharmaceutically acceptable acid addition salts can be administered before, simultaneously with or after the administration or intake of 1,4-benzodiazepines which have tranquillizing activity. If the compound of formula I or a pharmaceutically acceptable acid addition salt thereof is administered simultaneously with the 1,4-benzodiazepine which has tranquillizing activity, when the administration can be as an ad-hoc combination or in the form of a pharmaceutical combination which contains a compound of formula I or a pharmaceutically acceptable acid addition salt thereof and a 1,4-benzodiazepine derivative which has tranquillizing activity; such pharmaceutical combinations are likewise an object of the present invention. The dosage of the compounds of formula I and their pharmaceutically acceptable acid addition salts can vary within wide limits and is, of course, fitted to the individual requirements in each particular case. In general, a daily dosage of about 0.2 mg to about 500 mg should be appropriate.

As mentioned earlier, medicaments containing a compound of formula I or a pharmaceutically acceptable acid addition salt thereof are likewise an object of the present invention as is a process for the manufacture of such medicaments which comprises bringing one or more compounds of formula I or pharmaceutically acceptable acid addition salts thereof and, if desired, one or more other therapeutically valuable substances into a galenical administration form; in this connection reference is again made to the pharmaceutical combinations mentioned above which are likewise an object of the present invention. In particular, pharmaceutical combinations containing a compound of formula I and one of the schistosomicidally-active compounds mentioned above, especially (+)-5-(o-chlorophenyl)-1,3-dihydro-3-methyl-7-nitro-2H-1,4-benzodiazepin-2-one, are an object of the present invention. Such combinations are suitable for the control of schistosomiasis.

In the following Examples, which illustrate the present invention in more detail but in no way are intended to limit its extent, all temperatures are given in degrees Centigrade.

EXAMPLE 1

(a) 11.3 g of (0.057 mol) of 6-chloroisatoic acid anhydride and 5.78 g (0.057 mol) of L-azetidinecarboxylic acid are heated to 125° for 2 hours in 50 ml of dimethyl sulphoxide. Subsequently, the mixture is evaporated to dryness in a high vacuum and the residue obtained is heated to 150° for 2 hours. By chromatography on silica gel using ethyl acetate for the elution there is obtained (S)-5-chloro-1,10a-dihydroazeto[2,1-c][1,4]benzodiazepine-4,10(2H,9H)-dione of melting point 225°–228°.

(b) A suspension of 1.30 g (29.8 mmol) of sodium hydride (55 percent oil dispersion) in 40 ml of dry dimethylformamide is treated with 6.38 g (27 mmol) of (S)-5-chloro-1,10a-dihydroazeto[2,1-c][1,4]benzodiazepine-4,10(2H,9H)-dione at −15° and the mixture is stirred at this temperature for 0.5 hour. Subsequently, the mixture is cooled to −35° and treated dropwise with 4.8 ml (29.8 mmol) of diethylchlorophosphate.

In the meanwhile, a solution of 3.55 g (32.4 mmol) of potassium t-butylate in 14 ml of dry dimethylformamide is cooled in an acetone/dry-ice bath, treated with 4.1 ml (32.4 mmol) of ethyl isocyanoacetate and added dropwise at −10° to the mixture obtained according to the preceding paragraph. The cooling bath is removed, the mixture is stirred for about a further 15 minutes, neutralized with glacial acetic acid, poured into 100 ml of water and extracted three times with chloroform. The combined chloroform extracts are washed three times with water, dried over magnesium sulphate and evaporated. The crude product obtained is chromatographed on silica gel and subsequently recrystallized from ethyl acetate. There is obtained ethyl (S)-8-chloro-12,12a-dihydro-9-oxo-9H,11H-azeto[2,1-c]imidazo[1,5-a][1,4]benzodiazepine-1-carboxylate of melting point 184°–185°.

EXAMPLE 2

(a) A mixture of 1.79 g (5.4 mmol) of ethyl (S)-8-chloro-12,12a-dihydro-9-oxo-9H,11H-azeto[2,1-c]imidazo[1,5-a][1,4]benzodiazepine-1-carboxylate and 0.324 g (8.1 mmol) of sodium hydroxide is treated with 8.5 ml of water and 27 ml of ethanol and heated to boiling under reflux for 30 minutes. Subsequently, the mixture is neutralized with 8.1 ml of 1 N hydrochloric acid, the ethanol is distilled off, the residue is diluted with about 70 ml of water and left to stand in an ice-bath for 1 hour. The precipitated material is filtered off under suction, washed with water and dried. There is obtained (S)-8-chloro-12,12a-dihydro-9-oxo-9H,11H-azeto[2,1-c]imidazo[1,5-a][1,4]benzodiazepine-1-carboxylic acid of melting point 244°–245°.

(b) 0.92 g (3.0 mmol) of (S)-8-chloro-12,12a-dihydro-9-oxo-9H,11H-azeto[2,1-c]imidazo[1,5-a][1,4]benzodiazepine-1-carboxylic acid is heated with a bunsen burner until the gas evolution has ceased. The crude product is chromatographed on silica gel using chloroform/methanol (9:1) for the elution. After recrystallization from ethyl acetate/hexane, there is obtained (S)-8-chloro-12,12a-dihydro-9H,11H-azeto[2,1-c]imidazo[1,5-a][1,4]benzodiazepin-9-one of melting point 207°–208°.

EXAMPLE 3

(a) 16.3 g (0.1 mol) of isatoic acid anhydride and 10.1 g (0.1 mol) of L-azetidinecarboxylic acid are heated to 115° for 2 hours in 50 ml of dimethyl sulphoxide. Subsequently, the mixture is poured into 450 ml of water, cooled to 0° and the precipitated crystalline material is filtered off. There is obtained (S)-1,10a-dihydroazeto[2,1-c][1,4]benzodiazepine-4,10(2H,9H)-dione of melting point 217°–218°.

(b) A suspension of 1.03 g (23.7 mmol) of sodium hydride (55 percent oil dispersion) in 25 ml of dry dimethylformamide is treated with 4.0 g (19.8 mmol) of (S)-1,10a-dihydroazeto[2,1-c][1,4]benzodiazepine-4,10-(2H,9H)-dione at −10° to −20° and the mixture is stirred at this temperature for 45 minutes. The mixture is subsequently treated dropwise at −35° with 3.2 ml (19.8 mmol) of diethylchlorophosphate. The mixture is stirred at −20° for about a further 20 minutes.

In the meanwhile, a solution of 2.17 g (19.3 mmol) of potassium t-butylate in 7 ml of dry dimethylformamide is cooled in an acetone/dry-ice bath, treated with 2.5 ml (19.8 mmol) of ethyl isocyanoacetate and added dropwise at −15° to −10° to the mixture obtained according to the preceding paragraph. The cooling bath is removed, the mixture is neutralized after 15 minutes with glacial acetic acid, poured into 100 ml of water and extracted three times with chloroform. The chloroform extracts are washed three times with water, dried over magnesium sulphate and evaporated. The crude product obtained is chromatographed on a silica gel column. After recrystallization from ethyl acetate, there is obtained ethyl (S)-12,12a-dihydro-9-oxo-9H,11H-azeto[2,1-a]imidazo[1,5-a][1,4]-benzodiazepine-1-carboxylate of melting point 191°–194°.

EXAMPLE 4

(a) A suspension of 1.93 g (44.3 mmol) of sodium hydride (55 percent oil dispersion) in 45 ml of dry dimethylformamide is treated at −10° to −20° with 7.78 g (38.5 mmol) of (S)-1,10a-dihydroazeto[2,1-c][1,4]benzodiazepine-4,10(2H,9H)-dione. The mixture is stirred at −20° to −10° for 1.25 hours, treated dropwise with 7.2 ml (44.3 mmol) of diethylchlorophosphate at −35° and the mixture is stirred at this temperature for about a further 20 minutes.

In the meanwhile, a solution of 4.85 g (44.3 mmol) of potassium t-butylate in 15 ml of dry dimethylformamide is cooled in an acetone/dry-ice bath, treated with 6.26 g (44.3 mmol) of t-butyl isocyanoacetate and added dropwise at −15° to the mixture obtained according to the preceding paragraph. The cooling bath is removed, the mixture is stirred for a further 15 minutes, neutralized with glacial acetic acid, poured into 350 ml of water and extracted several times with chloroform. The chloroform extracts are washed three times with water, dried over magnesium sulphate and evaporated. By chromatography on silica gel using ethyl acetate/chloroform (1:3) for the elution and subsequent recrystallization of the resulting material from ethyl acetate/n-hexane there is obtained t-butyl (S)-12,12a-dihydro-9-oxo-9H,11H-azeto[2,1-c]imidazo[1,5-a][1,4]benzodiazepine-1-carboxylate of melting point 185°–187°.

(b) 1.77 g (5.4 mmol) of t-butyl (S)-12,12a-dihydro-9-oxo-9H,11H-azeto[2,1-c]imidazo[1,5-a][1,4]benzodiazepine-1-carboxylate are stirred in 14 ml of trifluoroacetic acid at 50° for 3 hours and at 65° for 3.5 hours. Subsequently, the mixture is evaporated to dryness and the residue is heated on a steam-bath for 2.5 hours in a high vacuum. The material is treated with ether, stirred for 1 hour while cooling with ice, the solid material is filtered off under suction while back-washing with ether and then dried. There is obtained (S)-12,12a-dihydro-9-oxo-9H,11H-azeto[2,1-c]imidazo[1,5-a][1,4]benzodiazepine-1-carboxylic acid of melting point 232°.

(c) 1.3 g (4.8 mmol) of (S)-12,12a-dihydro-9-oxo-9H,11H-azeto[2,1-c]imidazo[1,5-a][1,4]benzodiazepine-1-carboxylic acid are heated to 240° until the gas evolution ceases. After recrystallization from ethyl acetate, there is obtained (S)-12,12a-dihydro-9H,11H-azeto[2,1-c]imidazo[1,5-a][1,4]benzodiazepin-9-one of melting point 195°–197°.

EXAMPLE 5

0.54 g (2.4 mmol) of (S)-12,12a-dihydro-9H,11H-azeto[2,1-c]imidazo[1,5-a][1,4]benzodiazepin-9-one and 0.32 g (2.4 mmol) of N-chlorosuccinimide are treated with 10 ml of dimethylformamide and the mixture is stirred at 90° for 40 minutes. The mixture is poured into 50 ml of water and extracted four times with chloroform. The combined chloroform extracts are washed three times with water, dried over magnesium suphate and evaporated. The crude product is chromatographed on silica gel using chloroform/methanol (19:1) for the elution and subsequently recrystallized from ethyl acetate. There is obtained (S)-1-chloro-12,12a-dihydro-9H,11H-azeto[2,1-c]imidazo[1,5-a][1,4]benzodiazepin-9-one of melting point 210°–214°.

EXAMPLE 6

(a) 2.3 g (22.8 mmol) of azetidine-2-carboxylic acid and 3.72 g (22.8 mmol) of isatoic acid anhydride are treated with 20 ml of dimethyl sulphoxide, the mixture is stirred at 110° for 2 hours, subsequently poured into 250 ml of water and stirred for a further 2 hours. The precipitated material is filtered off under suction, washed with water and recrystallized from ethanol. There is obtained (R,S)-1,10a-dihydroazeto[2,1-c][1,4]benzodiazepine-4,10(2H,9H)-dione of melting point 250°–252°.

(b) 3.15 g (15.6 mmol) of (R,S)-1,10a-dihydroazeto[2,1-c][1,4]benzodiazepine-4,10(2H,9H)-dione are added to a suspension of 0.82 g (18.7 mmol) of sodium hydride (55 percent oil dispersion) in 25 ml of dry dimethylformamide. The mixture is stirred for 30 minutes and subsequently treated dropwise at −35° with 3 ml (18.7 mmol) of diethylchlorophosphate.

In the meanwhile, a solution of 2.05 g (18.7 mmol) of potassium t-butylate in 7 ml of dry dimethylformamide is cooled in an acetone/dry-ice bath, treated with 2.4 ml (18.7 mmol) of ethyl isocyanoacetate and added dropwise at −20° to −10° to the mixture obtained according to the preceding paragraph. Subsequently, the cooling bath is removed, the mixture is neutralized at room temperature with glacial acetic acid, poured into 200 ml of water and extracted four times with chloroform. The chloroform extracts are washed three times with water, dried over magnesium sulphate and evaporated. By chromatography on a silica gel column using ethyl acetate for the elution and subsequent recrystallization from ethyl acetate there is obtained ethyl (R,S)-12,12a-dihydro-9-oxo-9H,11H-azeto[2,1-c]imidazo[1,5-a][1,4]benzodiazepine-1-carboxylate of melting point 153°–154°.

Ethyl (S)-8-chloro-12,12a-dihydro-9-oxo-9H,11H-azeto[2,1-c]imidazo[1,5-a][1,4]benzodiazepine-1-carboxylate (active substance A) can be used as the active substance for the manufacture of pharmaceutical preparations as illustrated in Examples A to G:

EXAMPLE A

Tablets containing the following ingredients are manufactured in the usual manner:

|  | mg/tablet |
|---|---|
| Active substance A | 1 |
| Lactose | 103 |
| Maize starch | 25 |
| Microcrystalline cellulose | 70 |
| Magnesium stearate | 1 |
| Total | 200 |

EXAMPLE B

Capsules containing the following ingredients are manufactured:

|  | mg/capsule |
|---|---|
| Active substance A | 1 |
| Lactose | 164 |
| Maize starch | 30 |
| Talc | 5 |
| Total | 200 |

The active substance, lactose and maize starch are firstly mixed in a mixer and then in a comminuting machine. The mixture is returned to the mixer, the talc is added thereto and mixed thoroughly. The mixture is filled by machine into hard gelatine capsules.

EXAMPLE C

Injection solutions containing the following ingredients are manufactured:

|  | Per ml |  |
|---|---|---|
| Active substance A | 0.5 | mg |
| Benzyl alcohol | 0.015 | ml |
| Propyleneglycol | 0.4 | ml |
| Ethanol (95 percent) | 0.1 | ml |
| Sodium benzoate | 48.8 | mg |
| Benzoic acid | 1.2 | mg |
| Water for injection q.s. ad | 1.0 | ml |

For the manufacture of 10 000 ml of injection solution, 5 g of the active substance are dissolved in 150 ml of benzyl alcohol and 4000 ml of propyleneglycol and 1000 ml of ethanol are added thereto. Then, 12 g of benzoic acid are dissolved in the above mixture and there is added thereto a solution of 488 g of sodium benzoate in 300 ml of water for injection. The solution obtained is brought up to a volume of 10 000 ml by addition of water for injection, filtered and filled into ampoules of suitable size; the residual volume of the ampoules is filled with nitrogen, the ampoules are sealed and sterilized for 30 minutes in an autoclave at 0.7 atmosphere.

EXAMPLE D

Suppositories containing the following ingredients are manufactured:

|  | g/suppository |
|---|---|
| Active substance A | 0.001 |
| Cocoa butter (m.p. 36–37°) | 1.255 |
| Carnauba wax | 0.044 |
| Total | 1.3 |

The cocoa butter and carnauba wax are melted in a glass or steel vessel, mixed thoroughly and cooled to 45°. Thereupon, there is added thereto the finely powdered active substance and the mixture is stirred until it is completely dispersed. The mixture is poured into suppository moulds of suitable size, left to cool, the suppositories are removed from the moulds and packed individually in wax paper or metal foil.

EXAMPLE E

Capsules containing the following ingredients are manufactured:

|  | mg/capsule |
|---|---|
| Active substance A | 20.0 |
| (+)-5-(o-Chlorophenyl)-1,3-dihydro-3-methyl-7-nitro-2H-1,4-benzodiazepin-2-one (active substance B) | 30.0 |
| Lactose (crystalline) | 100.0 |
| Maize starch (white) | 27.5 |
| Talc | 10.0 |
| Magnesium stearate | 2.5 |
| Total | 190.0 |

The two active substances are mixed well with the adjuvants and 190.0 mg of the mixture are filled into interlocking capsules of suitable size.

EXAMPLE F

Tablets containing the following ingredients are manufactured:

|  | mg/tablet |
|---|---|
| Active substance A | 10.0 |
| (+)-5-(o-Chlorophenyl)-1,3-dihydro-3-methyl-7-nitro-2H-1,4-benzodiazepin-2-one (active substance B) | 30.0 |
| Lactose (powdered) | 15.0 |

-continued

|  | mg/tablet |
|---|---|
| Maize starch (white) | 19.5 |
| Povidon K30 | 3.5 |
| Maize starch (white) | 10.0 |
| Magnesium stearate | 2.0 |
| Total | 90.0 |

The two active substances, the powdered lactose and the first portion of white maize starch are mixed and sieved. This mixture is moistened with a solution of the Povidon K30 in water, kneaded, granulated, dried and sieved. The second portion of white maize starch and the magnesium stearate are added to the granulate. After mixing, the mass obtained is pressed to tablets weighing 90 mg.

EXAMPLE G

Tablets containing the following ingredients are manufactured:

|  | mg/tablet |
|---|---|
| Active substance A | 30 |
| (+)-5-(o-Chlorophenyl)-1,3-dihydro-3-methyl-7-nitro-2H-1,4-benzodiazepin-2-one | 30 |
| Lactose (powdered) | 22 |
| Maize starch (white) | 22 |
| Povidon K30 | 6 |
| Maize starch (white) | 16 |
| Magnesium stearate | 4 |
| Total | 130 |

The two active substances, the powdered lactose and the first portion of white maize starch are mixed and sieved. This mixture is moistened with a solution of the Povidon K30 in water, kneaded, granulated, dried and sieved. The second portion of white maize starch and the magnesium stearate are added to the granulate. After mixing, the mass obtained is pressed to tablets weighing 130 mg.

What is claimed:

1. A compound of the formula

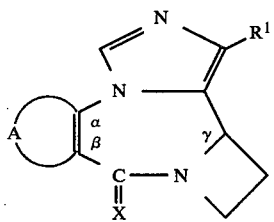

I wherein A together with the two carbon atoms denoted as α and β is the group

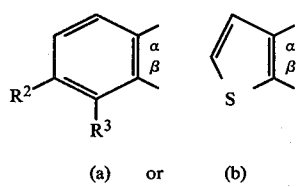

(a) or (b)

$R^1$ is hydrogen, lower alkyl, lower alkoxymethyl, halogen, nitro or a group of the formula —COOR$^4$, $R^2$ is hydrogen, trifluoromethyl or halogen, $R^3$ is hydrogen, trifluoromethyl, halogen or lower alkyl, $R^4$ is methyl, ethyl or isopropyl and X is an oxygen or sulphur atom and the carbon atom denoted as γ has the (S)- or (R,S)-configuration, and pharmaceutically acceptable acid addition salts thereof.

2. The compound of claim 1, wherein $R^1$ is hydrogen, chlorine or a group of the formula —COOR$^4$ in which $R^4$ is ethyl.

3. The compound of claim 2, wherein A is group (a), $R^2$ is hydrogen and $R^3$ is hydrogen or chlorine.

4. The compound of claim 3, wherein X is an oxygen atom.

5. The compound: ethyl (S)-8-chloro-12,12a-dihydro-9-oxo-9H,11H-azeto[2,1-c]imidazo[1,5-a][1,4]benzodiazepine-1-carboxylate.

6. A compound selected from the group consisting of Ethyl (R,S)-12,12a-dihydro-9-oxo-9H,11H-azeto[2,1-c]imidazo[1,5-a][1,4]benzodiazepine-1-carboxylate,
(S)-8-chloro-12,12a-dihydro-9H, 11H-azeto[2,1-c]imidazo[1,5-a][1,4]benzodiazepin-9-one,
ethyl (S)-12,12a-dihydro-9-oxo-9H,11H-azeto[2,1-c]imidazo[1,5-a][1,4]benzodiazepine-1-carboxylate
or
(S)-1-chloro-12,12a-dihydro-9H,11H-azeto[2,1-c]imidazo[1,5-a][1,4]benzodiazepin-9-one.

7. A method of antagonising in patients the central-depressant, muscle relaxant, ataxic, blood pressure-lowering and respiratory-depressant properties of 1,4-benzodiazepines having tranquilising activity which comprises daily administering to such patient from about 0.2 mg to about 500 mg of a compound of the formula

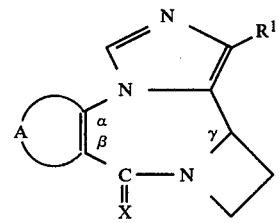

I wherein A together with the two carbon atoms denoted as α and β is the group

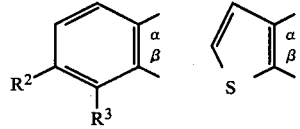

(a) or (b)

$R^1$ is hydrogen, lower alkyl, lower alkoxymethyl, halogen, nitro or a group of the formula —COOR$^4$, $R^2$ is hydrogen, trifluoromethyl or halogen, $R^3$ is hydrogen, trifluoromethyl, halogen or lower alkyl, $R^4$ is methyl, ethyl or isopropyl and X is an oxygen or sulphur atom and the carbon atom denoted as γ has the (S)- or (R,S)-configuration, or a pharmaceutically acceptable acid addition salt thereof.

8. The method of claim 7 wherein the 1,4-benzodiazepines are used to treat schistosomiasis.

* * * * *